US009931258B2

(12) United States Patent
Heimbrock et al.

(10) Patent No.: US 9,931,258 B2
(45) Date of Patent: Apr. 3, 2018

(54) MEDICAL LINE MANAGER

(71) Applicant: Hill-Rom Services, Inc., Batesville, IN (US)

(72) Inventors: Richard H. Heimbrock, Cincinnati, OH (US); Robert M. Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/296,767

(22) Filed: Oct. 18, 2016

(65) Prior Publication Data

US 2017/0035634 A1 Feb. 9, 2017

Related U.S. Application Data

(63) Continuation of application No. 12/547,054, filed on Aug. 25, 2009, now Pat. No. 9,486,374.

(51) Int. Cl.
| | |
|---|---|
| *A61G 7/05* | (2006.01) |
| *A61G 7/053* | (2006.01) |
| *A47C 21/08* | (2006.01) |
| *A61M 16/00* | (2006.01) |
| *A61M 5/14* | (2006.01) |

(52) U.S. Cl.
CPC .......... *A61G 7/0524* (2016.11); *A61G 7/0503* (2013.01); *A61G 7/0506* (2013.01); *A61G 7/0507* (2013.01); *A61G 7/0514* (2016.11); *A61M 5/1415* (2013.01); *A61M 16/0003* (2014.02); *A47C 21/08* (2013.01); *A61M 2209/082* (2013.01)

(58) Field of Classification Search
CPC .......... A61G 7/0507; A61G 2007/0524; A61G 2007/0509; A61G 2007/0513; A61G 2007/0514; A61G 7/0524; A61G 7/0509; A61G 7/0513; A61G 7/0514; A47C 21/08; F16L 3/01; F16L 3/02; F16L 3/06; F16L 3/10; F16L 3/00; F16M 13/02; F16M 13/00; F16M 13/005; F16M 11/041
USPC ................ 5/425, 428, 430, 658, 662, 503.1; 248/65, 68.1, 70, 75, 80, 176.1, 309.1
See application file for complete search history.

(56) References Cited

U.S. PATENT DOCUMENTS

| | | | | |
|---|---|---|---|---|
| 1,231,452 A | * | 6/1917 | Sword | A47B 96/1425 211/107 |
| 1,862,237 A | * | 6/1932 | Pepler | A47B 23/02 108/140 |
| 1,865,757 A | * | 7/1932 | Honsowetz | A47C 21/00 211/119.006 |
| 2,428,649 A | * | 10/1947 | Brown | A47C 21/003 362/144 |

(Continued)

*Primary Examiner* — Robert G Santos
(74) *Attorney, Agent, or Firm* — Barnes & Thornburg LLP

(57) ABSTRACT

A siderail assembly comprises a siderail and a medical line manager. The siderail includes a siderail body having a first surface, a second surface, and a side surface extending between about the first surface and about the second surface. The medical line manager is integrated into at least one of the first surface, the second surface, and the side surface of the siderail. The medical line manager includes a first side, a second side, and a bottom extending between about the first side and the second side. The medical line manager is configured to receive and removably retain at least one medical line therein.

17 Claims, 10 Drawing Sheets

(56) References Cited

U.S. PATENT DOCUMENTS

| | | | | |
|---|---|---|---|---|
| 2,662,715 A * | 12/1953 | McKnight | A47C 21/00 | 211/119.006 |
| 2,913,740 A * | 11/1959 | Eldridge | A61G 7/0503 | 174/135 |
| 3,338,538 A * | 8/1967 | Roche | A61G 7/0503 | 128/DIG. 26 |
| 4,141,524 A * | 2/1979 | Corvese, Jr. | A61G 7/0503 | 128/DIG. 26 |
| 4,262,872 A * | 4/1981 | Kodet | A61G 1/04 | 248/291.1 |
| 4,690,674 A * | 9/1987 | Dalglish | A61G 7/0503 | 128/DIG. 26 |
| 4,988,062 A * | 1/1991 | London | A61G 7/0503 | 128/DIG. 26 |
| 5,094,418 A * | 3/1992 | McBarnes, Jr. | A61G 7/0503 | 248/125.1 |
| 5,160,106 A * | 11/1992 | Monick | A61G 13/101 | 248/231.71 |
| 5,334,186 A * | 8/1994 | Alexander | A61M 5/1418 | 128/DIG. 15 |
| 5,337,430 A * | 8/1994 | Schlein | A61G 7/053 | 5/662 |
| 5,387,177 A * | 2/1995 | Dunn | A61G 7/05715 | 128/897 |
| 5,678,267 A * | 10/1997 | Kinder | A61G 7/0507 | 5/428 |
| 6,058,531 A * | 5/2000 | Carroll | A47C 21/08 | 5/428 |
| 6,728,985 B2 * | 5/2004 | Brooke | A61G 7/0507 | 5/430 |
| D503,231 S * | 3/2005 | Daugherty | D24/128 | |
| 7,039,971 B2 * | 5/2006 | Sebastien | A61G 7/053 | 5/430 |
| 7,357,772 B2 * | 4/2008 | McDermott | A61B 5/02055 | 600/22 |
| 7,766,289 B2 * | 8/2010 | Newkirk | A61G 7/018 | 248/176.1 |
| 7,805,789 B1 * | 10/2010 | Dean | A47C 21/08 | 5/646 |
| 7,850,595 B2 * | 12/2010 | White | A61G 7/0503 | 600/22 |
| 8,360,953 B2 * | 1/2013 | White | A61G 7/0503 | 600/22 |
| 8,370,977 B2 * | 2/2013 | Newkirk | A61G 7/018 | 248/176.1 |
| 8,578,531 B2 * | 11/2013 | Abernathey | A47C 31/00 | 5/424 |
| 9,486,374 B2 * | 11/2016 | Heimbrock | A61G 7/0503 | |
| 2003/0009952 A1 * | 1/2003 | Gallant | A61G 7/00 | 52/36.4 |
| 2003/0056293 A1 * | 3/2003 | Brooke | A61G 7/0507 | 5/662 |
| 2004/0186341 A1 * | 9/2004 | McDermott | A61B 5/02055 | 600/22 |
| 2005/0120485 A1 * | 6/2005 | Sebastien | A61G 7/053 | 5/662 |
| 2007/0181751 A1 * | 8/2007 | Newkirk | A61G 7/018 | 248/65 |
| 2008/0163425 A1 * | 7/2008 | White | A61G 7/0503 | 5/603 |
| 2010/0263123 A1 * | 10/2010 | Newkirk | A61G 7/018 | 5/503.1 |
| 2011/0010852 A1 * | 1/2011 | Heimbrock | A61G 7/0503 | 5/425 |
| 2011/0087064 A1 * | 4/2011 | White | A61G 7/0503 | 600/22 |
| 2011/0185507 A1 * | 8/2011 | Abernathey | A61G 7/053 | 5/662 |
| 2017/0035634 A1 * | 2/2017 | Heimbrock | A61G 7/0503 | |

* cited by examiner

MEDICAL LINE MANAGER

This Application claims priority to U.S. patent application Ser. No. 12/547,054 titled SIDERAIL WITH STORAGE AREA filed on Aug. 25, 2009 which is a continuation in part of U.S. patent application Ser. No. 12/589,536 titled SIDERAIL WITH STORAGE AREA filed on Jul. 15, 2009, the contents of which are incorporated herein by reference.

BACKGROUND OF THE DISCLOSURE

This disclosure relates generally to a person-support apparatus. More particularly, but not exclusively, one illustrative embodiment relates to a siderail that can be adapted to manage medical lines.

Patients in hospitals can have equipment connected to them by medical lines. Movement of the patient can cause the lines to move and get caught on the person-support apparatus or on other objects, which can result in disconnection of the line from the patient and/or equipment. While various person-support apparatuses have been developed, there is still room for improvement. Thus a need persists for further contributions in this area of technology.

SUMMARY OF THE DISCLOSURE

The present disclosure includes one or more of the features recited in the appended claims and/or the following features which, alone or in any combination, may comprise patentable subject matter.

One illustrative embodiment of the present disclosure can include a siderail having a medical line manager integrated therein that can be configured to receive at least one medical line and maintain the medical line within the medical line manager.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
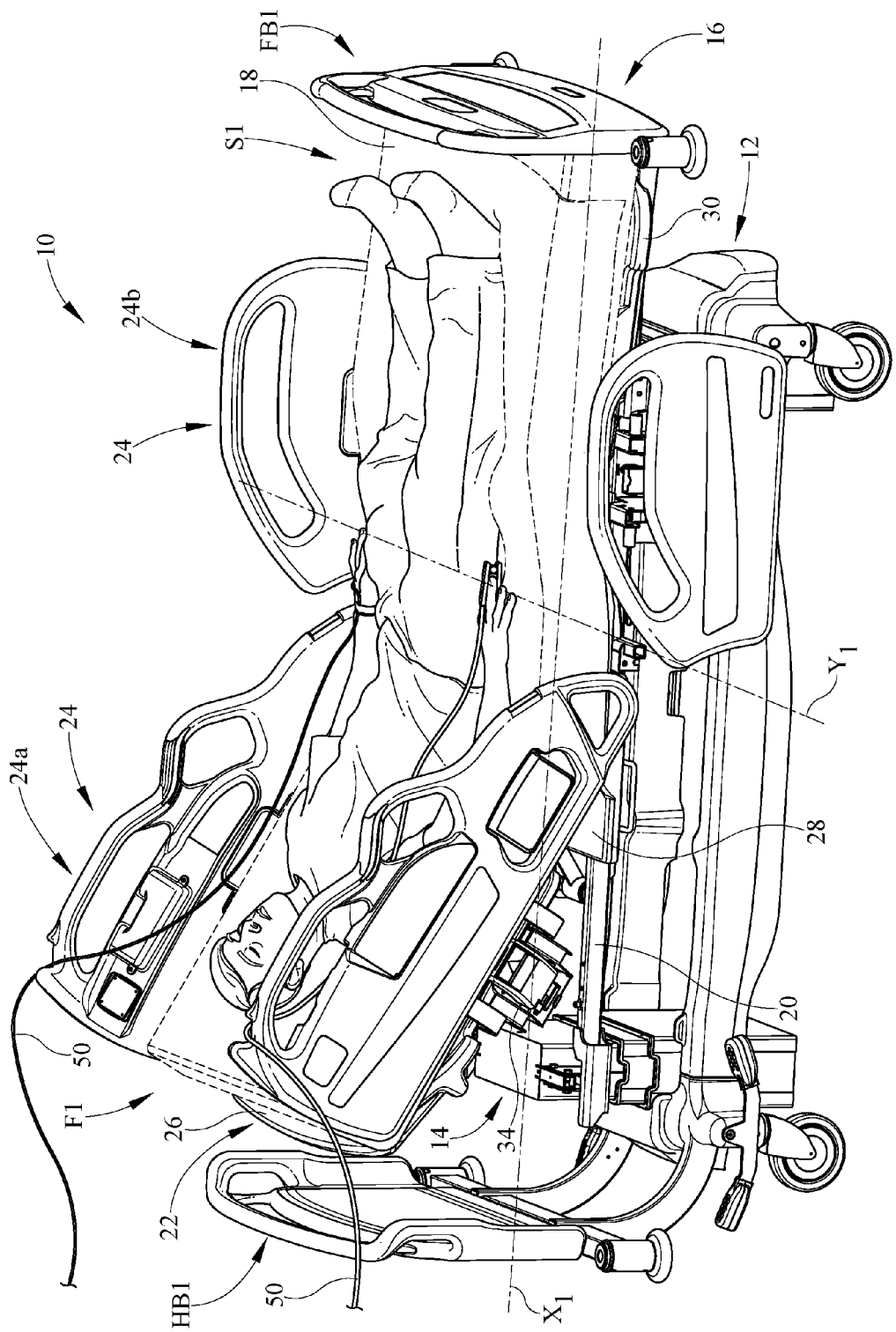
FIG. 1 is a perspective side view of a person-support apparatus including a frame with siderails coupled thereto according to one illustrative embodiment.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure can include a siderail having a medical line manager integrated therein that can be configured to receive at least one medical line and maintain the medical line within the medical line manager.

A person-support apparatus 10 according to one illustrative embodiment of the current disclosure is shown in FIG. 1. The person-support apparatus 10 can have a first section F1 or head support section F1, where the head of a person can be positioned, and a second section S1 or a foot support section S1, where the feet of the person can be positioned. It should be appreciated that the first section F1 and the second section S1 can be portions of the same section. In one illustrative embodiment, the person-support apparatus 10 can be a hospital bed. It should be appreciated that the person-support apparatus 10 can also be a hospital stretcher or an operating table. The person-support apparatus 10 can include a lower frame 12 or base 12, a plurality of supports 14 coupled with the lower frame 12, and an upper frame 16 supported on the supports 14 above the lower frame 12. It should be appreciated that the supports 14 can be lift mechanisms 14 that can move the upper frame 16 with respect to the lower frame 12. It should also be appreciated that in one illustrative embodiment the person-support apparatus 10 can support a person-support surface 18 thereon. It should be appreciated that the supports 14 can move the upper frame 16 to a Trendelenburg and/or a reverse Trendelenburg position with respect to the lower frame 12.

Figure 2:
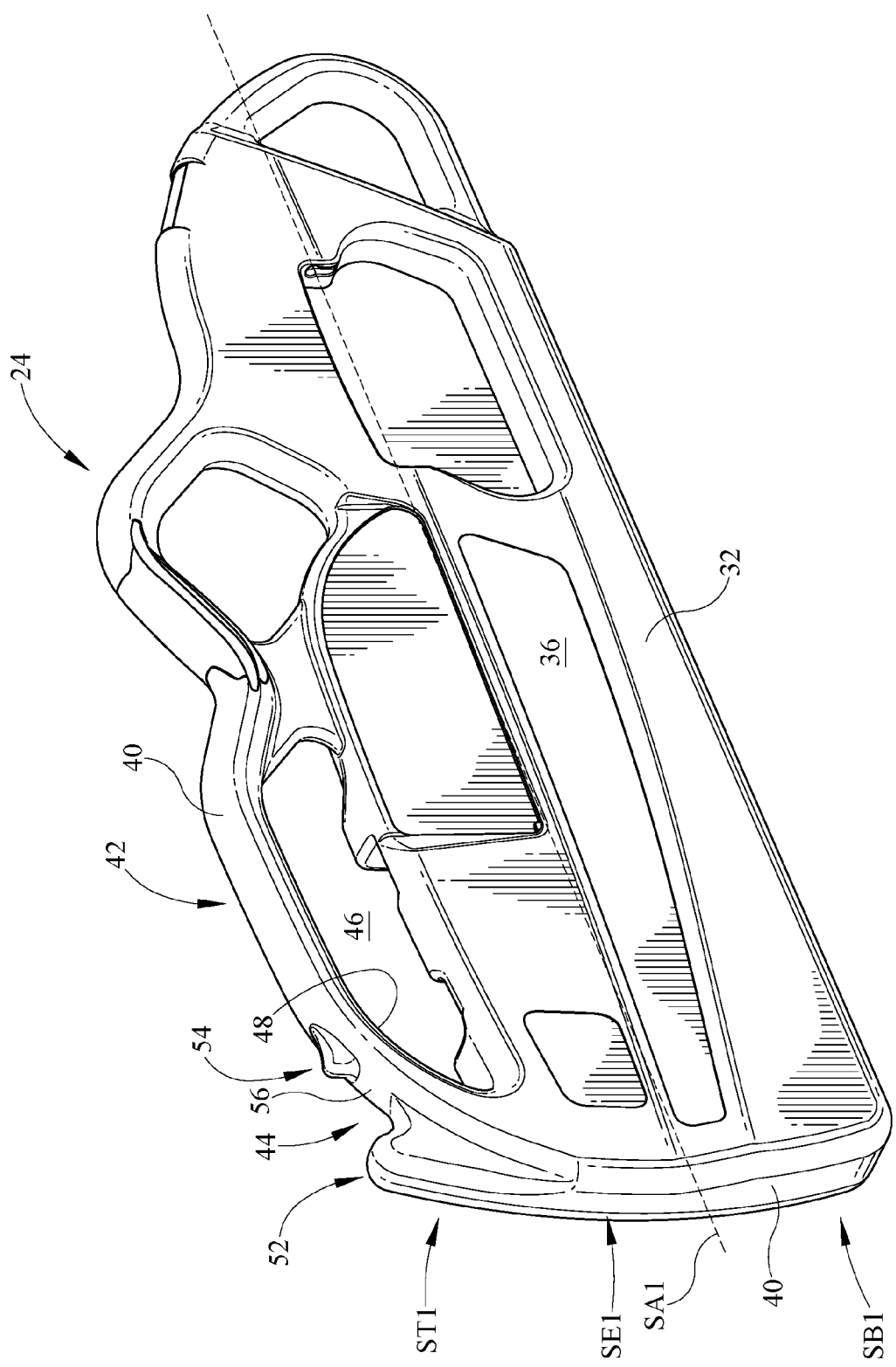
FIG. 2 is a perspective side view of the head siderail of FIG. 1 with a medical line manager integrated therein.

The upper frame 16 can define a longitudinal axis X1 and a lateral axis Y1 as shown in FIG. 1. The longitudinal axis X1 can extend at least the length of the person-support apparatus 10 through the first section F1 and the second section S1 along the lateral center of the upper frame 16. The lateral axis Y1 can be perpendicular the longitudinal axis X1 and extend at least the width of the person-support apparatus 10 through the longitudinal center of the upper frame 16. The upper frame 16 can include an intermediate frame 20, a deck 22, and siderails 24 as shown in FIGS. 1 and 2. It should be appreciated that the upper frame 16 can include endboards, for example, a headboard HB1 and a footboard FB1, coupled thereto. The intermediate frame 20 can be coupled with the supports 14 and can support the deck 22 thereon as shown in FIGS. 1 and 2. The deck 22 can include a head portion 26, a seat portion 28, and a foot portion 30. The head portion 26, the seat portion 28, and the foot portion 30 can be movably coupled with each other and the intermediate frame 20.

The siderails can define a siderail axis SX1 that can be parallel the longitudinal axis X1 as shown in FIGS. 1-9. The siderails 24 can include a siderail body 32 with a top portion ST1, a bottom portion SB1, an end portion SE1, and a siderail linkage 34 as shown in FIGS. 1-9. In one illustrative embodiment, the siderails 24 can have a thickness TS1 of less than 3 inches. it should be appreciated that the siderails 24 can have a thickness TS1 of between about 1.5 inches and about 2 inches.

The siderail linkage 34 can be coupled to the bottom portion SB1 of the siderail body 32 and can couple the siderails 24 to the deck 22 and/or the intermediate frame 20 as shown in FIG. 1. In one illustrative embodiment, the siderails 24 can be coupled to the head portion 26 of the deck 22 (i.e., a first siderail 24a or a head siderail 24a) and/or coupled to the foot portion 30 of the deck 22 and/or the intermediate frame 20 (i.e., a second siderail 24b or a foot siderail 24b) as shown in FIG. 1. The siderail linkage 34 can be configured to can facilitate movement of the siderails 24 between a deployed/operation position and a storage position. In the deployed/operation position, as shown in FIG. 1, at least a portion of the siderails 24 can be present above the upper frame 16. In the storage position, the siderails 24 can be moved to a lower position where at least a portion of the siderails 24 can be below the upper frame 16. It should be appreciated that the siderail linkage 34 can include a locking mechanism (not shown) that can maintain the siderails 24 in one of the operating and/or storage position when locked and can help facilitate movement of the siderails 24 between the operating and storage position when unlocked.

The siderail body 32 can include a first surface 36, a second surface 38, a third surface 40 or side surface 40 extending between the first surface 36 and the second surface 38, a grip portion 42, and a medical line manager 44 as shown in FIGS. 1-9. It should be appreciated that the siderail 24 can include a caregiver interface (not shown) that can be operable to control various functionalities of the person-support apparatus 10. At least a portion of the first surface 36 and the second surface 38 can be substantially parallel to one another. The first surface 36 can be oriented such that the first surface 36 faces toward the upper frame 16 and the second surface 38 can be oriented such that the second surface 38 faces away from the upper frame 16.

The grip portion 42 can be configured to be gripped by a person to assist the person with ingress/egress from the person support apparatus 10 as shown in FIGS. 1-9. In one illustrative embodiment, the grip portion 42 can be located along the top portion ST1 and can include a grip opening 46 that can pass through the siderail body 32 and define an inner surface 48 of the grip portion 42 as shown in FIGS. 1-9.

Figure 6:
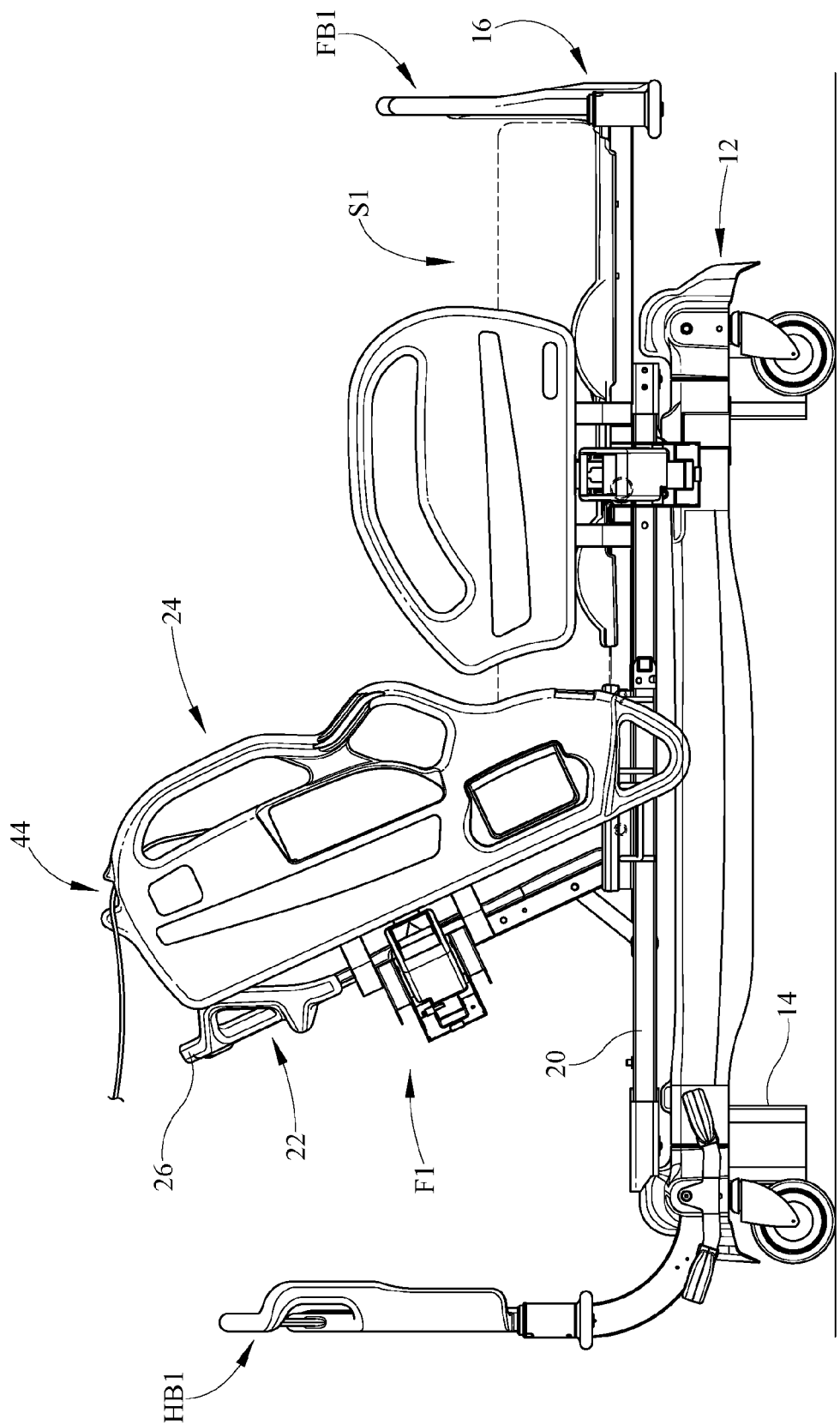
FIG. 6 is a side view of the person-support apparatus of FIG. 1 showing the medical line manager integrated at the end of the siderail of FIG. 1.
Figure 10:
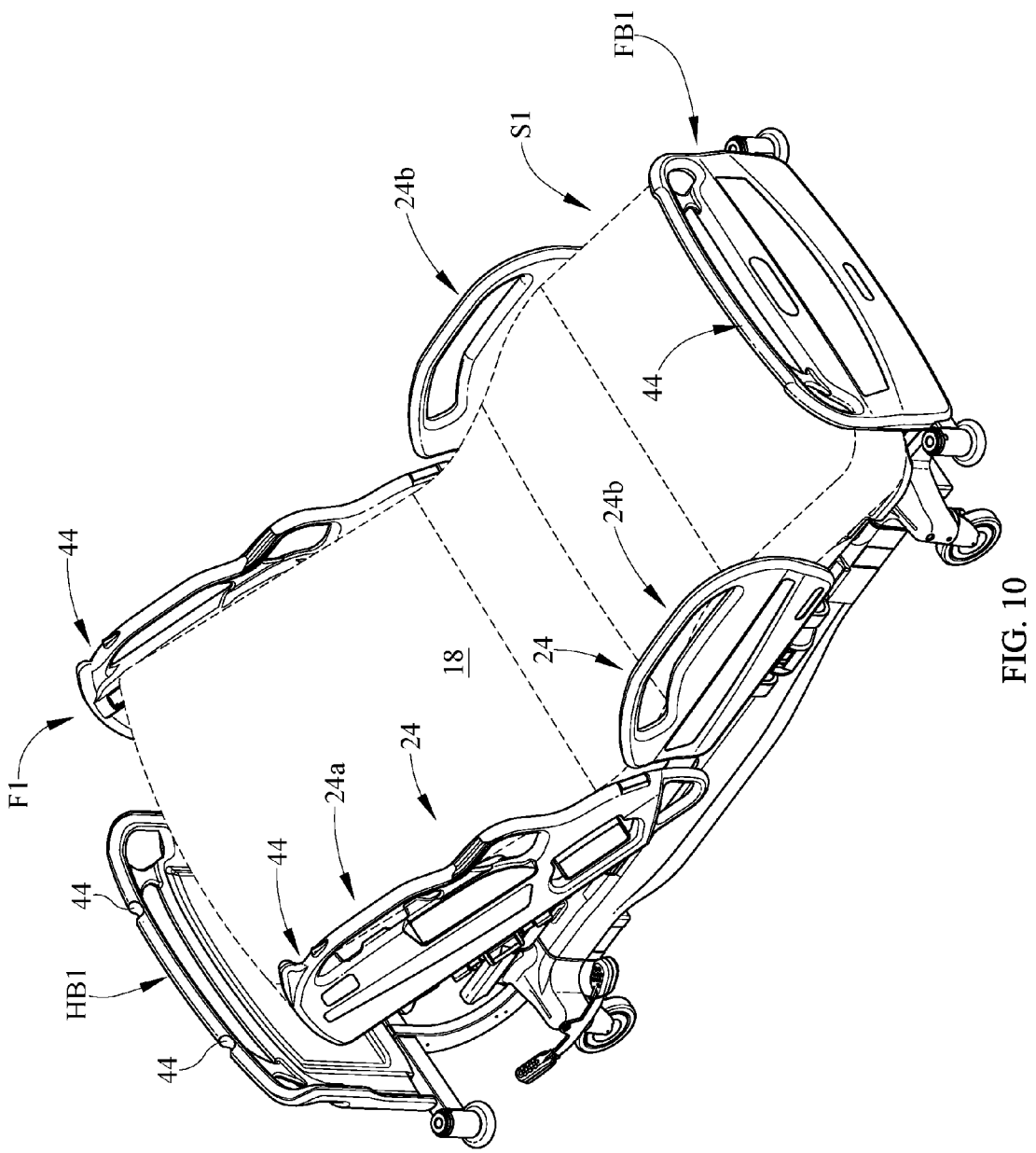
FIG. 10 is a perspective side view of a person-support apparatus with a medical line manager integrated into an endboard.

The medical line manager 44 can be integrated into the side surface 40 of the siderail 24 as shown in FIGS. 1-9. In one illustrative embodiment, the medical line manager 44 can be integrated into the side surface 40 along the top portion ST1 of the head siderail 24a as shown in FIGS. 1-5 and 7-9. In another illustrative embodiment, the medical line manager 44 can be integrated into the side surface 40 along the end portion SE1 of the siderail 24 as shown in FIG. 6. In yet another embodiment, the medical line manager 44 can be integrated into the side surface 40 along the top portion ST1 of the foot siderail 24b as shown in FIGS. 1-5 and 7-9. In still another embodiment, the medical line manager 44 can be integrated into a portion of the grip portion 42 as shown in FIGS. 1-5 and 7-9. It should be appreciated that more than one medical line manager 44 can be integrated into at least one of the side surface 40, the fist surface 36, and the second surface 38. It should also be appreciated that the medical line manager can be integrated into at least one of the first surface 36 and the second surface 38. It should further be appreciated that the medical line manager 44 can be integrated into at least one surface of at least one of the headboard HB1 and footboard FB1 as shown in FIG. 10.

The medical line manager 44 can be configured to receive and removably retain at least one medical line 50 therein. In one illustrative embodiment, the medical line manager 44 can be configured to removably retain between about 1 medical line 50 and about 8 medical lines 50. In another illustrative embodiment, the medical line manager 44 can be configured to removably retain at least about 4 IV's at about 28 FR (French) or about 0.367 inches. In yet another illustrative embodiment, the medical line 50 can have a diameter of less than about 1 inch in diameter. It should be appreciated that the medical line manager 44 can be configured to removably retain more or less medical lines 50, and/or larger or smaller medical lines 50. The medical line 50 can be or can include an intravenous line, an oxygen line, a catheter, cardiac lines, oxygen tubing, EKG/EEG/ECG electrodes, feed tubes, and other such medical tubing and medical wirings. In other illustrative embodiments, the medical line 50 can be cable wires 50, for example, power cables, monitor wires and other such wirings.

The medical line manager 44 can help reduce strain on the medical lines 50 and tangling of the medical lines 50. The medical line manager 44 can also be configured to allow for easy removal of the at least one medical line 50 in various situations, for example, when a patient is moved. It should be appreciated that the medical line manager 44 can assist in managing and organizing the at least one medical line 50 attached to the patient, and preventing the at least one medical line 50 from being disconnected from the patient and/or equipment.

Figure 3:
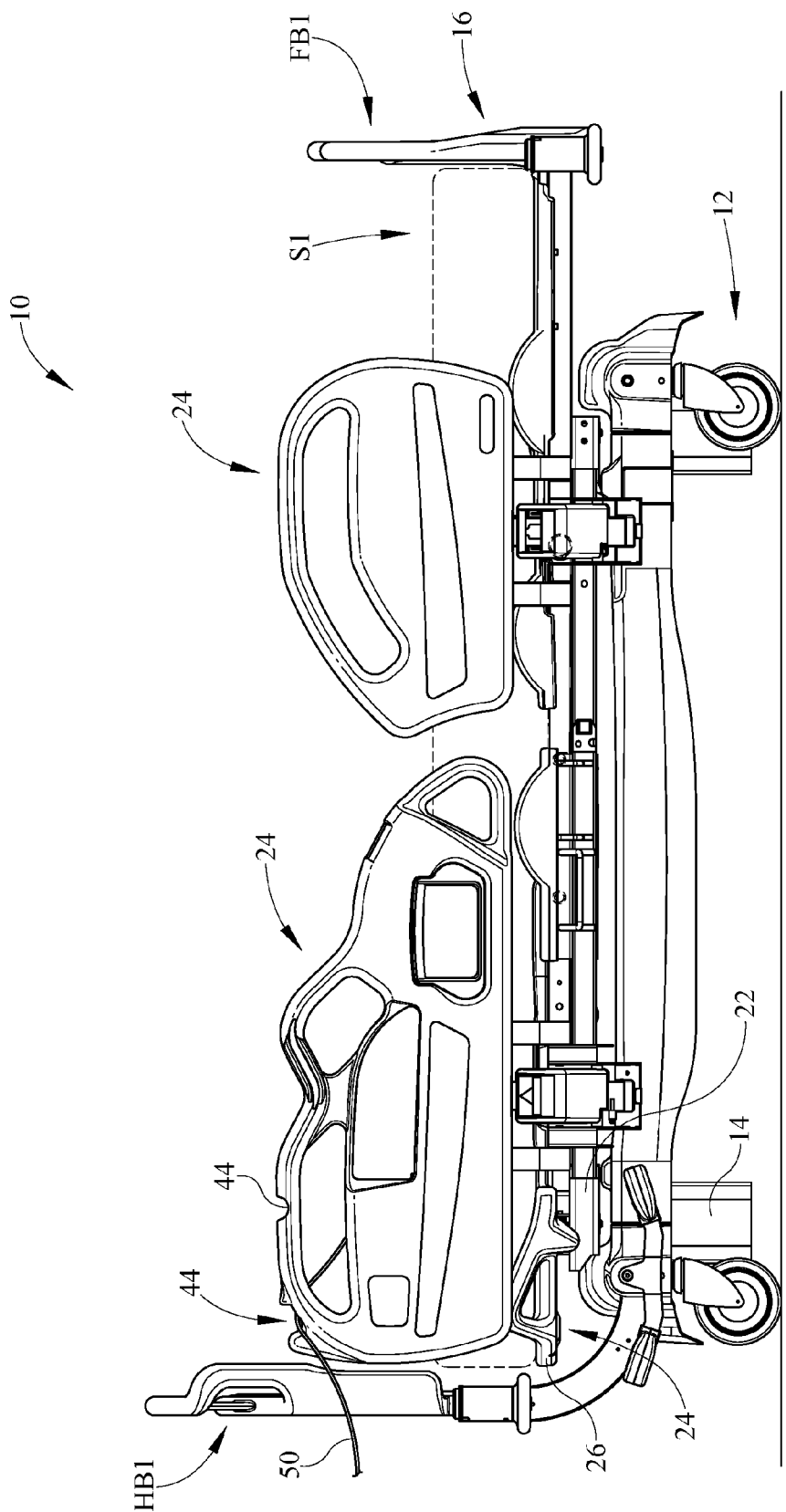
FIG. 3 is a perspective side view of the siderails of FIG. 1 with an integrated medical line manager in a head siderail according to another illustrative embodiment.

The medical line manager 44 can include a first end 52 or first side 52, a second end 54 or second side 54, and a base 56 or bottom 56 that can extend between the first end 52 and the second end 54 as shown in FIGS. 1-9. The first end 52 and the second end 54 can be defined by raised and recessed portions of the side surface 40. In one illustrative embodiment, the first end 52 and the second end 54 can be protrusions that can extend from the siderail 24. In another illustrative embodiment, the medical line manager 44 can be a groove as shown in FIG. 3. In yet another illustrative embodiment, the first end 52 can form a portion of the end portion SE1 of the siderail 24. In still other illustrative embodiments, the first end 52 and the second end 54 can be defined by a combination of raised and recessed portions. It should be appreciated that there may be more than one protrusion or recessed portion.

The first end 52 can be spaced apart from the second end 54 and can be oriented such that the first end 52 and the second end 54 are not horizontally co-planar as shown in FIGS. 1-9. It should be appreciated that the first end 52 and the second end 54 can be horizontally co-planar. In one illustrative embodiment, the first end 52 can be partially vertically below the second end 54 when the siderail axis SX1 is substantially parallel to the longitudinal axis X1, and the base 56 can be a length L1 at an angle A1 with respect to the siderail axis SX1. In another illustrative embodiment the base 56 can be about 2 inches long at an angle of about 33° with respect to the siderail axis SX1. In another illustrative embodiment, the base 56 can be angled such that the base 56 is tangent the inner surface 48 of the grip portion 42. It should be appreciated that the base 56 can be curved to mimic the inner surface 48 of the grip portion 42. It should also be appreciated that the base 56 can have a length of more or less than 2 inches.

The first end 52 can include a first engagement surface 58 and a transition portion 60 that can connect the first engagement surface 58 to the base 56 as shown in FIGS. 1-9. The first engagement surface 58 can form a first angle FA1 with respect to the base 56 and can have a first length FL1. In one illustrative embodiment, the first engagement surface 58 can form an angle of about 90° with respect to the base 56 (about 123° with respect to the siderail axis SX1) and can be about 0.7 inches long. In another illustrative embodiment, the first engagement surface 58 can form an angle of between about 127° and about 90° with respect to the base 56 (between about 160° and about 120° with respect to the siderail axis SX1). It should be appreciated that the first engagement surface 58 can form an angle of greater or less than about 90° with respect to the base 56 and can be more or less than about 0.7 inches in length.

The transition portions 60 can help prevent the medical lines 50 from catching or snagging on the medical line manager 44 as shown in FIGS. 1-9. In one illustrative embodiment the transition portions 60 can be curved as shown in FIGS. 1-9. It should be appreciated that the transition portions 60 can be ramps (not shown).

The first end 52 can extend a first distance FD1 from the base 56 and can have a first thickness FT1 as shown in FIGS. 1-9. In one illustrative embodiment, the first end 52 can extend at least about 1.4 inches from the base 56 and can have a thickness FT1 equal to the thickness TS1 of the siderail 24. It should be appreciated that the first end 52 can be thickness FT1 greater or less than the thickness TS1 of the siderail 24. It should also be appreciated that the thickness FT1 of the first end 52 can be less than about 3 inches. It should be appreciated that the first end 52 can extend more or less than 1.4 inches from the base 56.

At least a portion of the first end 52 can be curved as shown in FIGS. 1-9. In one illustrative embodiment, the first end 52 can have a radius of curvature of about half the first distance FD1. In another illustrative embodiment, the radius of curvature can be about 0.7 inches. It should be appreciated that at least a portion of the first end 52 can be longitudinally curved and/or laterally curved.

The second end 54 can include a second engagement surface 62 and a transition portion 64 that can connect the second engagement surface 62 to the base 56 as shown in FIGS. 1-9. The second engagement surface 62 can form a second angle SA1 with respect to the base 56 and have a second length SL1. In one illustrative embodiment, the second engagement surface 62 can form an angle of about 120° with respect to the base 56 (about 90° with respect to the siderail axis SX1) and can be less than about 0.6 inches long. In another illustrative embodiment, the second engagement surface 62 can form an angle of between about 120° and about 100° with respect to the base 56 (between about 90° and about 70° with respect to the siderail axis SX1). It should be appreciated that the second engagement surface 62 can form an angle of greater than about 120° or less than about 100° with respect to the base 56 (greater than about 90° or less than about 70° with respect to the siderail axis SX1) and can have a length of greater than about 0.6 inches.

The second end 54 can extend a second distance SD1 from the base 56 and can have a second thickness ST1 as shown in FIGS. 1-9. In one illustrative embodiment, the second end 54 can extend at least about 0.5 inches from the base 56 and can have a thickness ST1 that is less than the thickness TS1 of the siderail 24. It should be appreciated that the second end 54 can be a thickness ST1 that is greater or less than the thickness TS1 of the siderail 24. It should also be appreciated that the thickness ST1 of the second end 54 can be less than about 3 inches. It should also be appreciated that the thickness ST1 of the second end 54 can be between about 1.5 inches and 2 inches. It should also be appreciated that the second end 54 can extend more or less than 0.5 inches from the base 56.

Figure 4:
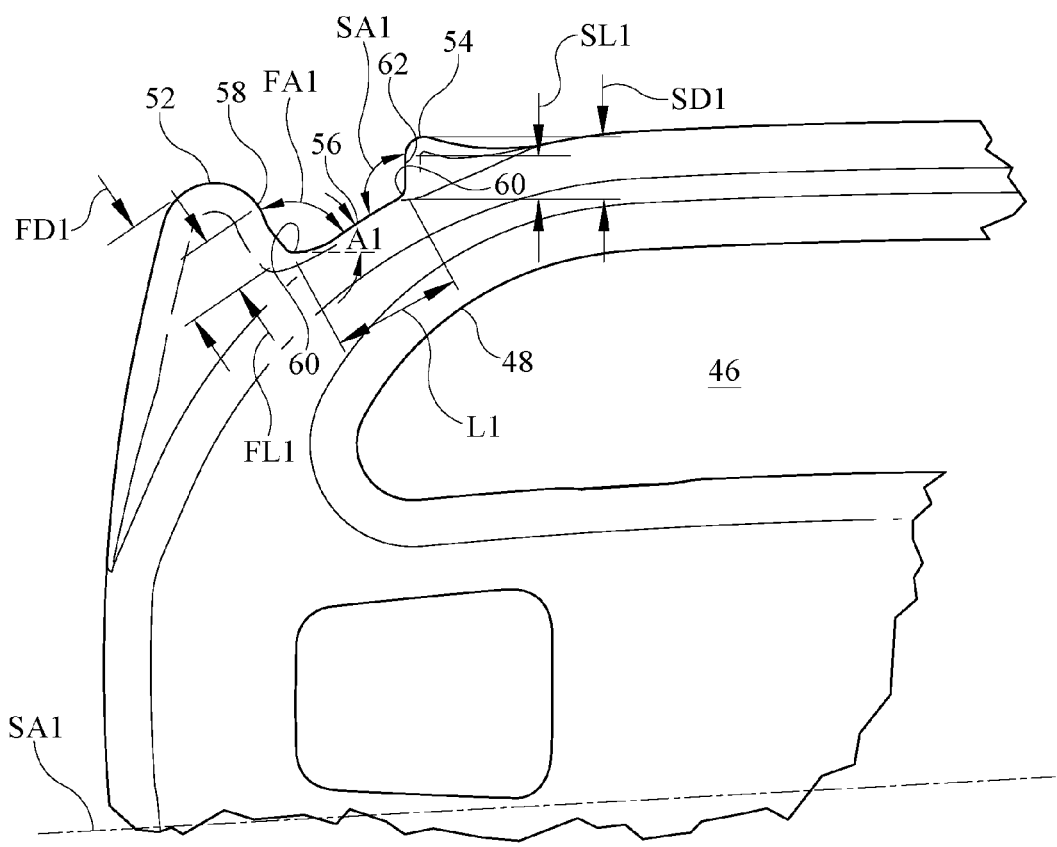
FIG. 4 is a side view of the medical line manager of FIG. 2.
Figure 5:
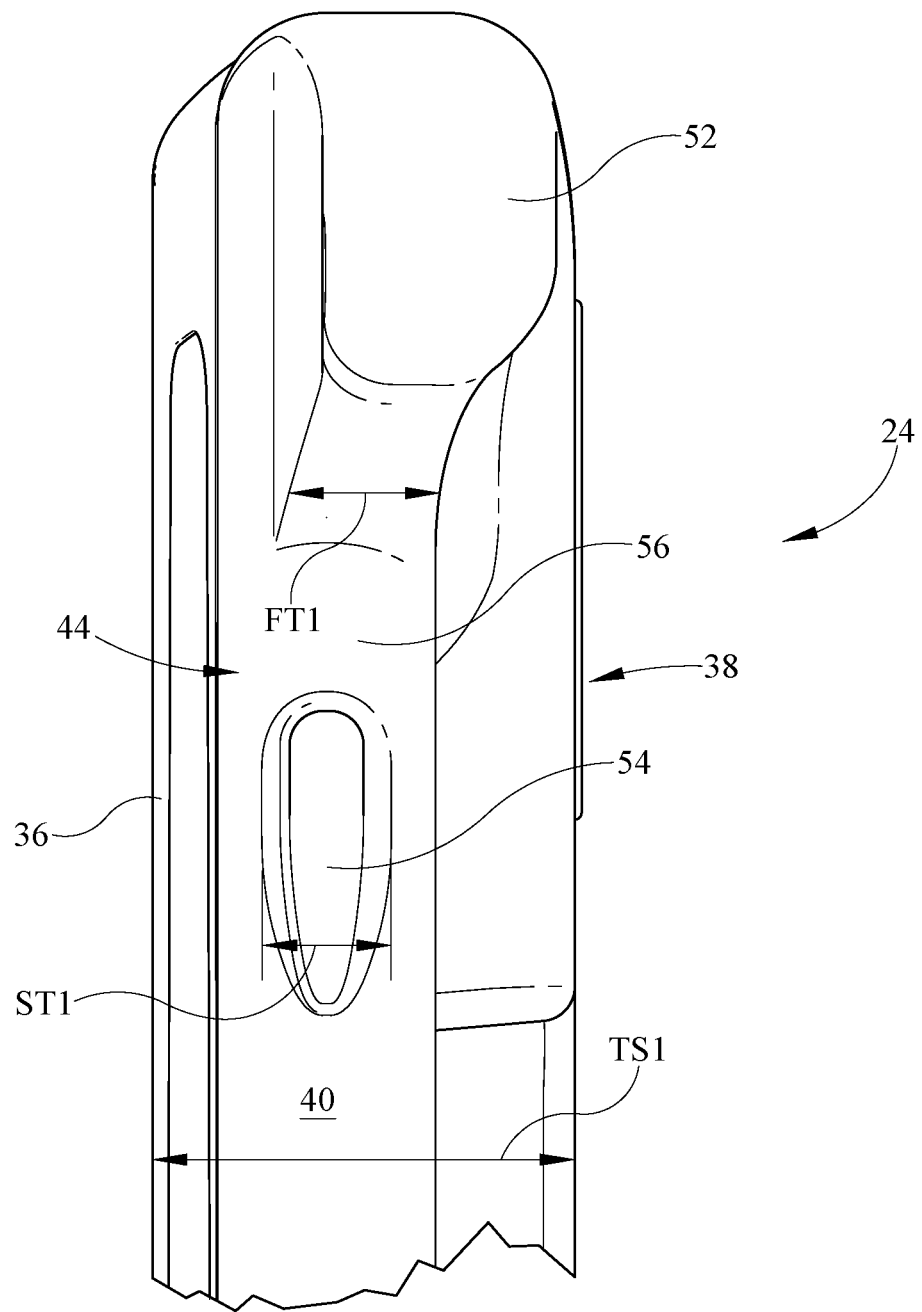
FIG. 5 is a top view of the medical line manager of FIG. 2.

At least a portion of the second end 54 can be curved as shown in FIGS. 1-9. In one illustrative embodiment, the second end 54 can have a radius of curvature of about half the second distance SD1. In another illustrative embodiment, the radius of curvature can be 0.25 inches. It should be appreciated that at least a portion of the second end 54 can be longitudinally curved and/or laterally curved as shown in FIGS. 3-4.

Figure 7:
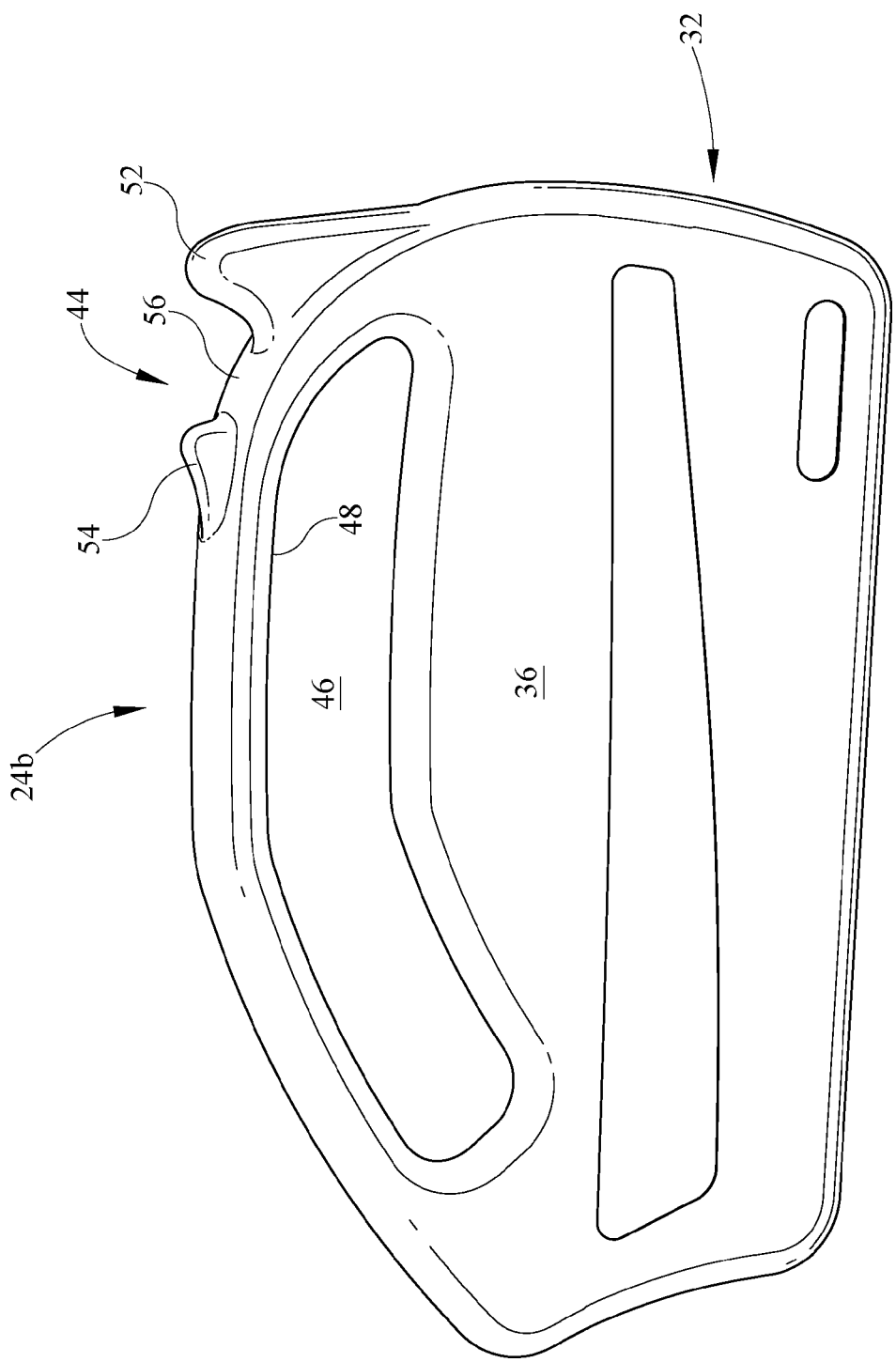
FIG. 7 is a side view of the siderails of FIG. 1 with the integrated medical line manager in a foot siderail.
Figure 8:
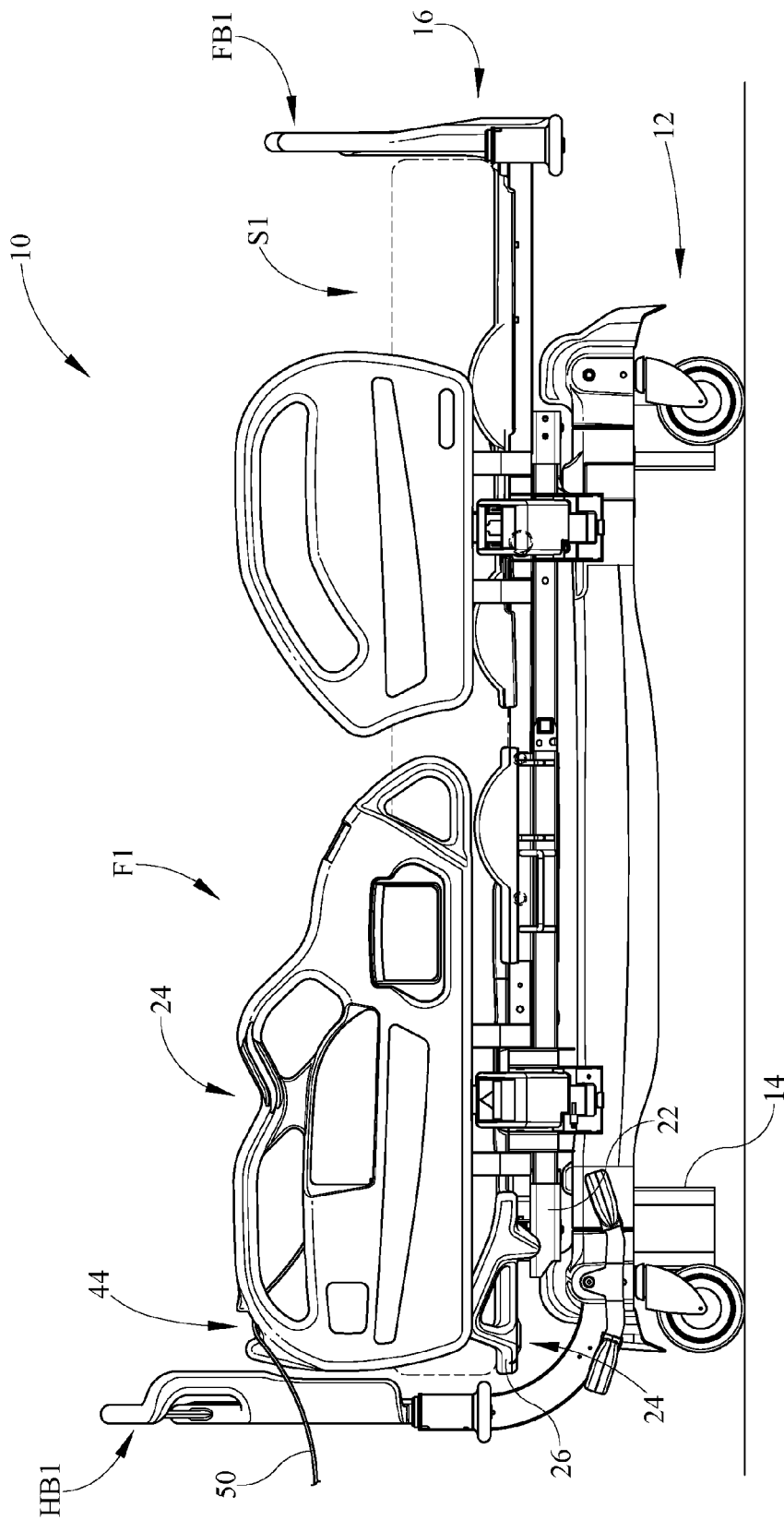
FIG. 8 is a side view of the siderails of FIG. 1 in a first position.
Figure 9:
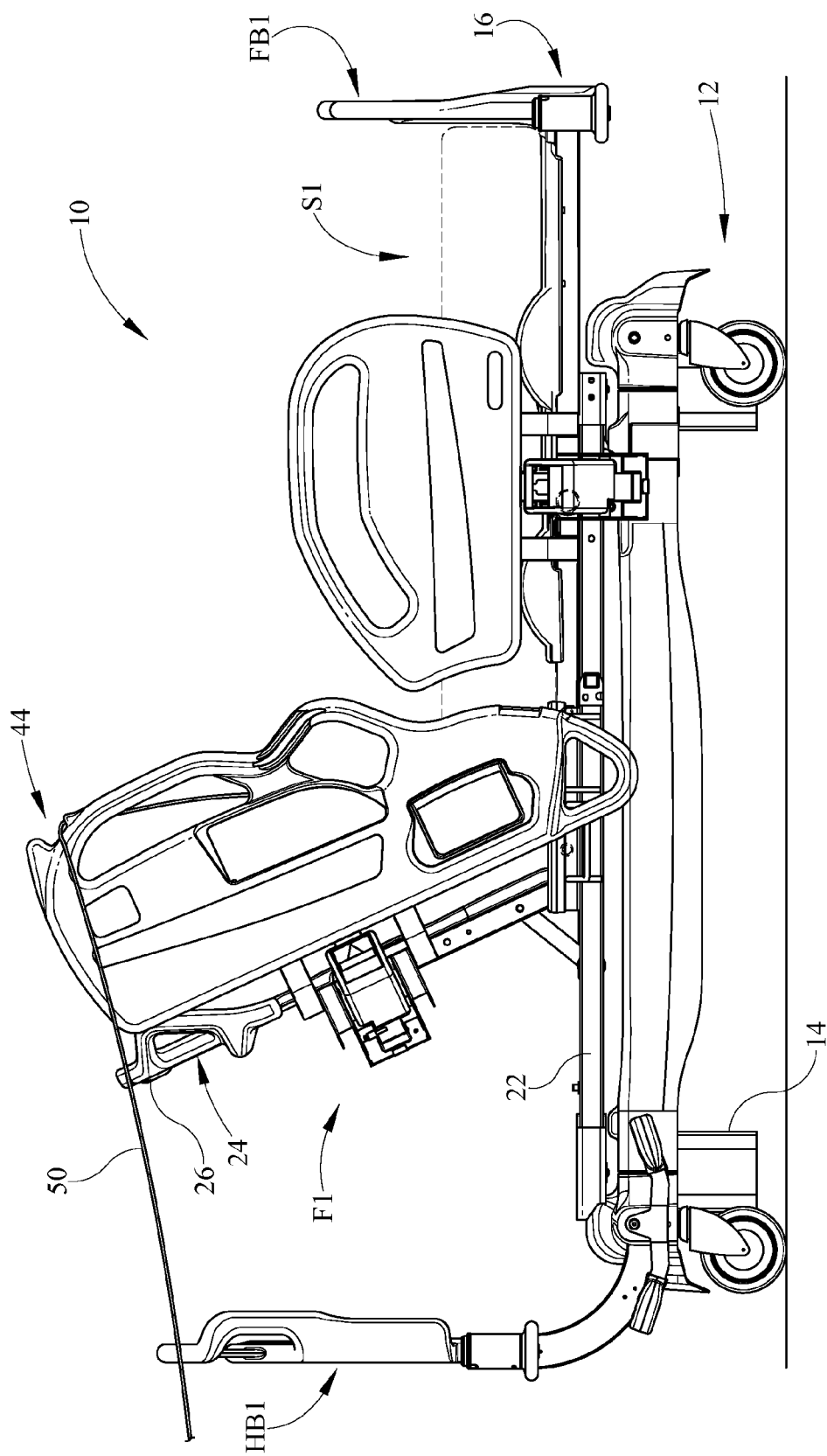
FIG. 9 is a side view of the siderails of FIG. 1 in a second position.

In operation, the medical line manager 44 can be in a first position where the first section F1 and the second section S1 are generally horizontal as shown in FIG. 6. At least one medical line 50 can be positioned within the medical line manager 44 and can engage at least one of the first end 52, second end 54, base 56, and the transition portions 58. As the first section F1 moves with respect to the second section S1, the medical line manager 44 can move from the first position to a second position as shown in FIG. 7. It should be appreciated that the first section F1 and the second section S1 can move with respect to horizontal to a second position, for example, Trendelenburg and reverse Trendelenburg. The medical line 50 can move within the medical line manager 44 between the first end 52 and the second end 54 and engage various portions of the medical line manager 44 to maintain the medical line 50 within the medical line manager 44.

To remove the medical line 50 from the medical line manager 44, the medical line 50 can be moved from between the first end 52 and the second end 54, for example, by being pulled or slid over the first end 52 or the second end 54. It should be appreciated that the medical line 50 can be lifted out from between the first end 52 or the second end 54 to remove the medical line 50 from the medical line manager 44.

Many other embodiments of the present disclosure are also envisioned. For example, a person-support apparatus comprises a frame and a siderail. The frame is configured to support a person thereon. The siderail is coupled to the frame. The siderail includes a siderail body with a first surface, a second surface, and a third surface extending between about the first surface and the second surface. The first surface is oriented such that the first surface faces toward the frame and the second surface is oriented such that the second surface faces away from the frame. The third surface includes a medical line manager configured to receive and removably retain at least one medical line therein.

In another example, a siderail assembly comprises a siderail and a medical line manager. The siderail includes a siderail body having a first surface, a second surface, and a side surface extending between about the first surface and about the second surface. The medical line manager is integrated into at least one of the first surface, the second surface, and the side surface of the siderail. The medical line manager includes a first side, a second side, and a bottom extending between about the first side and the second side. The medical line manager is configured to receive and removably retain at least one medical line therein.

In yet another example, a person-support apparatus comprises a frame, an endboard, a siderail, and a medical line manager. The frame includes a first end and a second end with a longitudinal axis extending through the first end and the second end and a lateral axis substantially perpendicular to the longitudinal axis. The endboard is coupled to at least one of the first end and the second end of the frame. The siderail is coupled to a frame. The medical line manager is integrated into at least one of the endboard and the siderail. The medical line manager including a first side, a second side, and a bottom extending between about the first side and about the second side, the medical line manager is configured to receive and removably retain at least one medical line therein.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof; or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A person-support apparatus, comprising:
a frame configured to support a person thereon;
a siderail coupled to the frame, the siderail including a siderail body with a first surface, a second surface, and a third surface extending between the first surface and the second surface, the first surface being oriented such that the first surface faces toward the frame and the second surface being oriented such that the second surface faces away from the frame, the third surface including a medical line manager configured to receive and removably retain at least one medical line therein;
a headboard coupled to the frame, the headboard including a medical line manager integrated into a surface of the headboard;
wherein the medical line manager of the siderail includes a first side, a second side, and a bottom extending between the first side and the second side, the medical line manager being configured to receive and removably retain at least one medical line therein wherein at least one of the first side and the second side protrudes from the at least one of the first surface, the second surface, and the third surface;
wherein the siderail includes a movement mechanism coupled to the siderail body and configured to rotate the siderail body between a deployed position and a storage position; and
a grip portion including an opening passing through the first surface and the second surface and cooperating with the third surface to define a grip.

2. The person-support apparatus of claim 1, wherein the medical line manager of the headboard includes a first side, a second side, and a bottom extending between the first side and the second side, the medical line manager being configured to receive and removably retain at least one medical line therein.

3. The person-support apparatus of claim 2, wherein the medical line manager of the siderail includes a first side, a second side, and a bottom extending between about the first side and about the second side, the medical line manager being configured to receive and removably retain at least one medical line therein.

4. The person-support apparatus of claim 3, wherein the siderail includes a plurality of medical line managers and each of the plurality of medical line managers of the siderail includes a first side, a second side, and a bottom extending between about the first side and about the second side, the medical line managers each being configured to receive and removably retain at least one medical line therein and wherein at least a portion of one of the plurality of medical line managers extends from a surface of the siderail.

5. The person-support apparatus of claim 2, wherein the siderail includes a plurality of medical line managers and each of the plurality of medical line managers of the siderail includes a first side, a second side, and a bottom extending between about the first side and about the second side, the medical line managers each being configured to receive and removably retain at least one medical line therein and wherein at least a portion of one of the plurality of medical line managers extends from a surface of the siderail.

6. The person-support apparatus of claim 1, wherein the headboard includes a plurality of medical line managers integrated into a surface of the headboard.

7. A person-support apparatus, comprising:
a frame configured to support a person thereon;
a siderail coupled to the frame, the siderail including a medical line manager integrated into a surface of the siderail and configured to receive and removably retain at least one medical line therein;
the siderail including a siderail body with a first surface, a second surface, and a third surface extending between the first surface and the second surface; and
a grip portion including an opening passing through the first surface and the second surface and cooperating with the third surface to define a grip.

8. The person-support apparatus of claim 7, further comprising at least one of a headboard or a footboard coupled to the frame, wherein the at least one headboard or footboard includes a plurality of medical line managers integrated into a surface of the at least one headboard or footboard.

9. The person-support apparatus of claim 8, wherein the medical line manager of the siderail includes a first side, a second side, and a bottom extending between about the first side and about the second side, the medical line manager being configured to receive and removably retain at least one medical line therein wherein at least one of the first side and the second side protrudes from the at least one of the first surface, the second surface, and the side surface.

10. The person-support apparatus of claim 8, wherein the medical line manager of the siderail includes a first side, a second side, and a bottom extending between about the first side and about the second side, the medical line manager being configured to receive and removably retain at least one medical line therein.

11. The person-support apparatus of claim 7, wherein the medical line manager of the siderail includes a first side, a second side, and a bottom extending between about the first side and about the second side, the medical line manager being configured to receive and removably retain at least one medical line therein wherein at least one of the first side and the second side protrudes from the at least one of the first surface, the second surface, and the side surface.

12. The person-support apparatus of claim 11, wherein the medical line manager of the at least one headboard or footboard includes a first side, a second side, and a bottom extending between about the first side and about the second side, the medical line manager being configured to receive and removably retain at least one medical line therein.

13. The person-support apparatus of claim 7, wherein the medical line manager of the siderail includes a first side, a second side, and a bottom extending between about the first side and about the second side, the medical line manager being configured to receive and removably retain at least one medical line therein.

14. The person-support apparatus of claim 12, wherein the at least one headboard or footboard includes a plurality of medical line managers and each of the plurality of medical line managers of the headboard or footboard includes a first side, a second side, and a bottom extending between the first side and the second side, the medical line managers each being configured to receive and removably retain at least one medical line therein.

15. The person-support apparatus of claim 13, wherein the siderail includes a plurality of medical line managers and each of the plurality of medical line managers of the siderail includes a first side, a second side, and a bottom extending between about the first side and about the second side, the medical line managers each being configured to receive and removably retain at least one medical line therein and wherein at least a portion of one of the plurality of medical line managers extends from a surface of the siderail.

16. The person-support apparatus of claim 13, wherein the siderail includes a plurality of medical line managers and each of the plurality of medical line managers of the siderail includes a first side, a second side, and a bottom extending between about the first side and about the second side, the medical line managers each being configured to receive and removably retain at least one medical line therein.

17. The person-support apparatus of claim 7, further comprising at least one of a headboard or a footboard coupled to the frame, wherein the at least one headboard or footboard includes a plurality of medical line managers integrated into a surface of the at least one headboard or footboard, wherein the at least one headboard or footboard includes a plurality of medical line managers and each of the plurality of medical line managers of the at least one headboard or footboard includes a first side, a second side, and a bottom extending between the first side and the second side, the medical line managers each being configured to receive and removably retain at least one medical line therein, and wherein the siderail includes a plurality of medical line managers and each of the plurality of medical line managers of the siderail includes a first side, a second side, and a bottom extending between the first side and the second side, the medical line managers each being configured to receive and removably retain at least one medical line therein and wherein at least a portion of one of the plurality of medical line managers extends from a surface of the siderail.

* * * * *